United States Patent
Hofstetter et al.

(10) Patent No.: US 8,426,667 B2
(45) Date of Patent: Apr. 23, 2013

(54) MEDICAL COMPRESS II

(75) Inventors: Juergen Hofstetter, Heidenheim (DE); Horst Schmid, Sontheim (DE); Rainer Halbauer, Obergroeningen (DE)

(73) Assignee: Paul Hartmann AG, Heidenheim (DE)

( * ) Notice: Subject to any disclaimer, the term of this patent is extended or adjusted under 35 U.S.C. 154(b) by 496 days.

(21) Appl. No.: 12/452,861

(22) PCT Filed: Jul. 12, 2008

(86) PCT No.: PCT/EP2008/005717
§ 371 (c)(1),
(2), (4) Date: Apr. 12, 2010

(87) PCT Pub. No.: WO2009/015757
PCT Pub. Date: Feb. 5, 2009

(65) Prior Publication Data
US 2010/0198126 A1    Aug. 5, 2010

(30) Foreign Application Priority Data
Aug. 1, 2007   (DE) .................. 10 2007 036 082

(51) Int. Cl.
*A61F 15/00*   (2006.01)

(52) U.S. Cl.
USPC ................. 602/44; 602/75; 128/855

(58) Field of Classification Search ............. 602/41–54, 602/75; 128/849–856
See application file for complete search history.

(56) References Cited

U.S. PATENT DOCUMENTS

| 3,421,502 | A | * | 1/1969 | St. Clair ................ 206/440 |
| 4,984,570 | A | * | 1/1991 | Langen et al. ............ 602/44 |
| 5,045,080 | A |   | 9/1991 | Dyer |
| 5,052,381 | A |   | 10/1991 | Gilbert |
| 5,575,781 | A |   | 11/1996 | DeBusk |

FOREIGN PATENT DOCUMENTS

| BE | 505 633 | 1/1953 |
| DE | 22 61 889 | 3/1973 |
| DE | 90 14 500 | 2/1991 |
| DE | 10 2005 053 149 | 5/2007 |
| EP | 1 782 782 | 5/2007 |
| GB | 782 861 | 9/1957 |
| GB | 1 410 810 | 10/1975 |

\* cited by examiner

*Primary Examiner* — Michael A. Brown
(74) *Attorney, Agent, or Firm* — Paul Vincent (57) ABSTRACT

Medical compresses, especially gauze compresses, are proposed which can be especially advantageously folded and stacked.

20 Claims, 5 Drawing Sheets

MEDICAL COMPRESS II

This application is the national stage of PCT/EP2008/005717 filed on Jul. 12, 2008 and claims Paris Convention Priority to DE 10 2007 036 082.9 filed Aug. 1, 2007.

BACKGROUND OF THE INVENTION

The invention relates to medical compresses made of a textile web material, especially gauze compresses, in a user-friendly form. The invention further relates to a method for manufacturing such compresses.

Medical compresses have been known for the treatment of acute wounds in emergency medicine or for use in surgical interventions for a long time. These compresses essentially differ by the material used and are thus divided into gauze compresses and nonwoven compresses. Gauze compresses are usually made of a cotton fabric that has a coarse or fine lattice structure depending on the thread density. The requirements of the gauze in the formation of compresses are defined in DIN EN 14079.

Because the gauze compresses have a lattice structure, which has the drawback that terminal threads can come loose, many solutions have been proposed to prevent this detachment. For example, DE 2261889 describes a compress that has at least one meshed strip. The meshing of the threads forms two borders lying opposite each other from which no threads can become detached. The compress is constituted by a partial section of this strip material, wherein the cut edges of this section are folded in. Moreover, DE 9014500 proposes a gauze compress that has thermoplastic threads, tapes, strips, or nonwoven strips in the immediate vicinity of a cut edge. These additional materials are welded, heat-sealed, or glued to the gauze. For example, compresses with folded-in edges have become established on the market as a known type of gauze compress. These proposed solutions or existing products have the common feature that they are seen as too complicated and/or costly to manufacture.

The object of this invention is to provide alternative, textile, medical compresses that provide a high degree of reliability in use while being inexpensive to manufacture. Moreover, a plurality of such compresses should be easy to stack, wherein the compresses should occupy the smallest possible packaging volume. In addition, a method is to be provided to manufacture these compresses.

SUMMARY OF THE INVENTION

These objectives are achieved by a medical compress and a method for manufacture thereof according to the independent claims, wherein an inventive medical compress comprises at least 8 layers of a textile web material, with each layer being connected to a further layer by at least one folded edge, and at least two folded edges are perpendicular to each other. The compress is constituted by a rectangular material section of the web material with two parallel cut edges A located opposite each other and two parallel cut edges B located opposite each other, wherein the edge length a of the cut edges A is greater than the edge length b of the cut edges B. The compress is folded in such a way that the compress comprises a first enclosing edge formed from at least one first folded edge and one second folded edge, wherein the first folded edge connects directly adjacent layers or partial sections of the directly adjacent layers and is formed parallel with the cut edges B, and the second folded edge connects the outer layers forming the contact surfaces of the compress. The first enclosing edge preferably comprises at least two, in particular, four first folded edges connecting directly adjacent layers.

In the context of this invention, a folded edge denotes an edge or partial section of the edge that is formed by completely or partially laying upon one another, folding upon one another, or folding-in two different subunits of the material section, wherein the two subunits of the material section are connected by means of the folded edge. Herein, the two subunits of the material section can be directly adjacent after the laying upon one another, folding upon one another, or folding-in, which means that the two subunits of the material section are in direct contact, or are separated by further layers. If the partial sections laid or folded upon one another are separated by at least one further layer, this is referred to as an enclosing edge in the context of this invention. The enclosing edge is constituted by at least one cut edge and/or at least one folded edge and the folded edge that is different from this cut or folded edge and that connects the partial sections laid or folded upon one another, wherein the edges involved lie directly along or against one another. The outside folded edges connecting the two partial sections laid or folded upon one another thus enclose the inside cut edges and/or folded edges, wherein the enclosing edge is constituted by the cut and/or folded edge and the folded edge connecting the partial sections laid or folded upon one another. Ideally, the outside folded edge and the inside cut, and/or folded edges lie directly along or against one another. In this case, there is no distance between the edges. However, the cut and/or folded edges can be held at a distance from the folded edge connecting the partial sections laid or folded upon one another by further enclosing edges. In connection with this invention, the term enclosing edges also refers to edges whose participating cut and/or folded edges are at a slight distance, that is, no more than 10%, from the outside folded edge. In this case, the value of the distance is referred to the length of a marginal edge of the compress in the folded condition, wherein the marginal edge of the compress that has the greatest edge length is used as the basis for measurement.

A cut edge of a material section of the web material, by contrast, is an edge that is constituted by separation of a first material section from a larger material section comprising the first material section, wherein the first material section has one cut edge and the remaining material section also has one cut edge. This separation can be effected by all separation techniques known today, such as cutting with knifes or scissors, laser beams, water jets, and other techniques.

Further, an abutting edge denotes a cut or folded edge as well as partial sections of these cut or folded edges that are formed by the placing of this cut or folded edge or these partial sections of the cut or folded edges against a further cut edge or a further folded edge or partial sections of the further cut edge or further folded edge, wherein the participating cut or folded edges or the partial sections thereof are located in one plane. Ideally, the abutting edges of an inventive compress lie directly along or against each other. In this case, there is no distance between the edges. According to this invention, the term abutting edges also refers to edges whose participating cut or folded edges are at a slight distance, that is, no more than 15%, from each other and/or overlap by up to 15%, wherein the value of the distance or overlap refers to the length of a marginal edge of the compress in the final folded condition, wherein the marginal edge of the compress that has the greatest edge length is used as the basis for measurement.

Moreover, in the context of this invention, a marginal edge also refers to an outer edge of the final folded compress (unless indicated otherwise).

By the constitution of an inventive enclosing edge that forms a marginal edge of the final folded compress, a compress can be provided that has no exposed cut edges and also saves material and thus reduces production costs. The constitution of an enclosing edge from folded edges prevents threads from becoming detached from a cut edge and from entering a wound during use for the intended purpose. Moreover, an inventive compress has the advantage that even if the completed at least 8-ply compress is unfolded once no cut edges are exposed. This compress is especially safe to handle and is user-friendly because the user can decide whether to use the 8-ply compress, for example, as a 4-ply compress or as an 8-ply compress. In both cases, no cut edges are exposed, that is, each cut edge of the material section is covered by at least one layer of material.

A compress can basically be manufactured from a rectangular material section of a web material with two parallel cut edges A located opposite each other and two parallel cut edges B located opposite each other, wherein the edge length a of the cut edges A is greater than the edge length b of the cut edges B. In formation of a compress with an inventive enclosing edge that comprises at least a first folded edge that is formed parallel with the smaller cut edges B, and one folded edge that encloses this first folded edge, a considerable material saving can be achieved over a compress with one enclosing edge that comprises a first folded edge that is formed parallel with the larger cut edges A and an enclosing edge that encloses this first folded edge. For example, this material saving amounts to 5 to 15% for a square, 8-ply compress with the same material depending on the contact surface and the width of the first folded-over partial sections.

It has also proven advantageous if the compress is folded in such a way that the outer layers forming the contact surfaces of the compress have the shape of a rectangle or a square. In particular, the medical compress is folded in such a way that the outer layers forming the contact surfaces of the compress are each completely constituted by a contiguous area of the web material. These layers forming the contact surfaces therefore do not have abutting edges. In particular, the medical compress is folded in such a way that the outer layers forming the contact surfaces of the compress are each completely constituted by a contiguous area of the web material, wherein the contact surfaces are rectangular or square. In a highly preferred embodiment, the compress is folded in such a way that all marginal edges of the final folded compress are constituted by folded edges or enclosing edges.

These contact surfaces can be implemented by manufacturing an inventive compress from a rectangular material section of the web material with two parallel cut edges A located opposite each other and two parallel cut edges B located opposite each other, wherein the edge length a of the cut edges A is larger than the edge length b of the cut edges B, and each cut, folded, abutting, enclosing and/or marginal edge of the compress is formed parallel or perpendicular to a further cut, folded, abutting, enclosing and/or marginal edge of the compress and wherein at least one cut, folded, enclosing or abutting edge of the compress is formed perpendicular to a further cut, folded, enclosing or abutting edge of the compress. In a further preferred embodiment, the folded edges that are formed parallel with the cut edges B of the material section constitute the first folded edges. In yet a further preferred embodiment, the folded edges that are formed parallel with the cut edges B of the material section constitute the folded edges that form the first enclosing edge of the final folded compress together with a further folded edge of the compress, wherein in a highly preferred embodiment, the cut edges A constitute the first abutting edges of the compress. These folded edges formed parallel with the cut edges B connect two directly adjacent layers of the compress. On the other hand, the further folded edge connects the two layers forming the contact surfaces of the compress. In a highly preferred embodiment, the folded edges that are formed parallel with the cut edges B of the material section constitute the first folded edges, wherein these first folded edges constitute the first enclosing edge of the final folded compress together with the further folded edge, wherein in a highly preferred embodiment, the cut edges A constitute first abutting edges of the compress. In this case, partial sections of the cut edges B can preferably be disposed so as to be completely coextensive within the compress when the compress is viewed from above.

In this way, an inventive compress preferably also has rectangular or square contact surfaces with the marginal edges C and D, wherein the edge length c of the marginal edges C is greater than or equal to the edge length d of the marginal edges D, and is preferably folded in such a way that partial sections of the cut edges B of the compress are disposed so as to be coextensive when viewed from above and, in particular, to be parallel with the marginal edges D. In particular, an inventive compress has square contact surfaces F with marginal edges D with edge length d. However, an inventive compress can also have rectangular contact surfaces with the marginal edges C and D, wherein the edge length c of the marginal edge C is greater than the edge length d of the marginal edge D, and has first folded edges and further folded edges parallel with the marginal edge D as the enclosing edge. In this case, the cut edges A of the rectangular material section are parallel with the marginal edges C and the cut edges B of the rectangular material section are parallel with the marginal edges D. It must be noted at this point that inventive compresses can be manufactured both by machine and by hand.

In a further preferred embodiment, the compress according to the claims has at least 8 and no more than 12 layers. In particular, the inventive compress is a compress that has at least a first 8-ply region and a second 10- or 12-ply region as seen in cross-section. In this case, the compress does not have a homogeneous layer structure over its entire transverse or longitudinal extent as seen in cross-section but the compress is 10- or 12-ply in a first partial region and 8-ply in at least one further partial region. In particular, the compress has a first 8-ply marginal region and a second 12-ply marginal region. However, it is possible for the compress to have a first 8-ply, and a second 8-ply marginal region that is different from the first, and a 10-ply central region. Moreover, the compress can have a homogeneous layer structure of either 10 or 12 layers.

According to a special embodiment of this invention, each marginal edge of the compress is constituted exclusively by folded edges and/or enclosing edges. These compresses have the advantage that they are especially safe to use. This configuration of the folded edges also has the advantage of a minimum probability of grasping into the compress. That means that even if the inventive compresses are disposed in a stack, a compress can be grasped without unintentionally grasping a further layer of an adjacent compress. This is, in particular, the case if a compress has marginal edges, for example, that contain cut edges of the underlying material section.

In a further embodiment of the invention, the compress comprises two further cut and/or folded edges as abutting edges. In particular, these abutting edges are parallel with the second folded edge. It is further preferred if the abutting edges are perpendicular to the enclosing edge. In a highly preferred embodiment, the compress is folded in such a way that the cut edges A or the partial areas of the cut edges A are constituted as abutting edges. This ensures that all cut edges are disposed inside the compress. This can also ensure, in particular, that all marginal edges of the compress are constituted by folded edges.

According to a further embodiment of this invention, the cut edges B or a partial section of the cut edges B have, at every point, a distance from the parallel first enclosing edge of at least 15% and no more than 85% of the length of a marginal edge that is perpendicular to the first enclosing edge. In an especially preferred embodiment, the compress has cut edges B or a partial section thereof that has, at every point, a distance from a parallel first enclosing edge of at least 20% and no more than 60% of the length of a marginal edge that is perpendicular to the first enclosing edge. In a highly preferred embodiment, these compresses have cut edges B or a partial section of the cut edges B that at every point have a distance from a parallel first enclosing edge of at least 20% and no more than 40% of the length of a marginal edge that is perpendicular to the first enclosing edge.

Any textile web material other than nonwoven web materials, so-called nonwovens, can be used to manufacture an inventive compress. This invention does not relate to any nonwoven compresses. According to the invention, in particular, wovens or knitteds can be used as the textile web materials. In a highly preferred embodiment, wovens and, in particular, wovens with a plain weave are used.

The textile web materials can further preferably be manufactured from a yarn or fiber material, which includes fibers or filaments of natural origin and/or synthetic fibers. Among fibers of natural origin, an inventive compress comprises, in particular, fibers made of cotton, hemp, flax, or linen. If the web material comprises yarn or fiber material that comprises synthetic fibers, fiber or filaments of viscose, polyester, cellulose acetate, carboxymethylcellulose, hydroxyethylcellulose can be used. The textile web material highly preferably comprises a yarn or fiber material made of cotton and/or viscose that meets the requirements of DIN EN 14079. These materials, in particular, gauze, cannot be processed by a stepless, continuous method, unlike the known non-textile or nonwoven web materials. For that reason, inventive compresses have to be made of a discrete material section.

One highly preferred embodiment of an inventive medical compress is a gauze compress. This gauze compress comprises at least 8 layers of gauze according to DIN EN 14079, wherein each layer is connected to a further layer by at least one folded edge and wherein at least one first folded edge and one second folded edge are perpendicular to one another. The gauze compress is folded in such a way that the compress comprises at least two folded edges as first abutting edges, wherein each of these first abutting edges connects directly adjacent layers. In particular, the medical compress has two folded edges as first abutting edges and two cut edges as second abutting edges. Moreover, this gauze compress can comprise all further characteristics of the type described above, individually or combined.

This invention thus provides a compress that is folded in such a way that the folded-in cut edges are superposed at the margin as on known folded-edge compresses. However, unlike these folded-edge compresses, inventive compresses have only 12 layers in this marginal region and not 16 layers, as folded-edge compresses have. A compress is therefore provided that is flatter and thus occupies less space. Due to the inventive manner of folding, it is now possible to provide a compress that can be stacked more easily.

In a further conception of this invention, a stack of compresses comprising a plurality of inventive medical compresses is also the object of this invention. This stack comprises a plurality of compresses of the type described above. In particular, this stack can comprise a plurality of identical compresses, wherein each compress has individual characteristics or combinations of characteristics of the compresses described above.

In particular, therefore, a stack of compresses comprising a plurality of medical compresses comprising at least 8 layers of a textile web material, in particular a plurality of gauze compresses comprising at least 8 layers of gauze according to DIN EN 14079 is also the object of this invention. Each of these at least 8 layers of each individual compress is connected via at least one folded edge with a further layer of this compress, wherein at least two folded edges are perpendicular to each other. The compress is constituted by a rectangular material section of the web material with two parallel cut edges A located opposite each other and two parallel cut edges B located opposite each other, wherein the edge length a of the cut edges A is greater than the edge length b of the cut edges B. The compress is folded in such a way that the compress comprises a first enclosing edge formed from at least one first folded edge and one second folded edge, wherein the first folded edge connects directly adjacent layers or partial sections of the directly adjacent layers and is formed parallel with the cut edges B, and the second folded edge connects the outside layers forming the contact surfaces of the compress. The first enclosing edge preferably comprises at least two, in particular, four, first folded edges connecting directly adjacent layers.

Due to the configuration of folded edges as a first enclosing edge, a stack of compresses can be provided that is more stable and occupies less space than the compresses available on the market. In this way, in particular, packaging material can be saved. For example, if folded-edged compresses available on the market are stacked, a pack containing a stack of compresses with 100 compresses has a height of 155 mm (outer dimension of the packaging). On the other hand, if inventive compresses are stacked (100 items) under the same conditions, the outer dimension is 139 mm (the same measurement conditions). In this way, in particular, packaging material and storage space can be saved.

Moreover, an inventive stack preferably has compresses with rectangular or square contact surfaces, wherein each compress has two marginal edges C of edge length c opposite each other and two marginal edges D of edge length d opposite each other, and wherein edge length c is greater than or equal to edge length d. In particular, this stack has a plurality of compresses with square contact surfaces.

In a further embodiment of this invention, an inventive stack of compresses has a plurality of compresses that are constituted by a rectangular material section of a textile web material with two parallel cut edges A located opposite each other and two parallel cut edges B located opposite each other, wherein the edge length a of the cut edges A is greater than the edge length b of the cut edges B. An inventive stack of compresses highly preferably comprises a plurality of compresses whose cut edges B or partial sections of the cut edges B has, at every point, a distance from a parallel first enclosing edge of at least 15% and no more than 85% of the length of a second marginal edge perpendicular to the first enclosing edge.

These compresses are stacked one upon the other in such a way that in each case a first contact surface of a first compress lies coextensively on a first contact surface of a second or further compress. Each first enclosing edge of each compress that comprises a folded edge formed with the cut edges B and a further folded edge, connecting the two outer layers forming the contact surfaces of the compress of the web material, can further preferably lie coextensively upon the same enclosing edge of the second or further compress.

In a further development of the invention, a method for the manufacture of a medical compress with at least 8 layers of a textile web material, wherein each layer is connected to further layers by at least one folded edge and at least two folded edges are perpendicular to each other, is also the object of this invention. In particular, a method for the manufacture of a compress of the type described above is provided. The method comprises the method steps a) Provision of a rectangular material section of the web material with two first cut edges A lying opposite each other and two cut edges B lying opposite each other, wherein the edge length a of the cut edge A is larger than the edge length b of the cut edge B, b) Folding-in of the cut edges B of the rectangular material section along a first fold line parallel with the cut edge B and a second fold line parallel with the cut edge B to constitute two first folded edges, c) Folding-in of at least one of the folded edges constituted under b) along a third fold line lying parallel with a cut edge B to constitute a further folded edge or an enclosing edge, d) Folding-in of the folded edge or enclosing edge constituted under c) along a fourth fold line lying parallel with a cut edge B to constitute a first enclosing edge that comprises at least a first folded edge and a second folded edge and e) Further folding-in of cut edges or formed folded or folded-in edges to constitute abutting edges or further folded or folded-in edges.

In particular, within the method step e), folding-in of the first cut edges A of the rectangular material section is performed to constitute two abutting edges.

Furthermore, within the method step b), folding-in of the first cut edges B of the rectangular material section is preferably performed, wherein each fold line has, at every point, a distance of at least 5 mm and no more than 30 mm from the nearest cut edge B.

The inventive method is, in particular, intended to provide a method for manufacturing a medical compress that comprises at least 8 and no more than 12 layers of a web material. In a highly preferred embodiment, the inventive method is a method for manufacturing a compress that has at least one first 8-ply region and one second 10- or 12-ply region as seen in cross-section. In this case, the compress does not have a homogeneous layer structure over its entire transverse or longitudinal extent as seen in cross-section but the compress is 10- or 12-ply in a first partial region and 8-ply in at least one further partial region. In particular, the compress has a first 8-ply marginal region and a second 12-ply marginal region. However, it is possible for the compress to have a first 8-ply, and a second 8-ply marginal region that is different from the first, and a 10-ply central region. Moreover, the compress can have a homogeneous layer structure of either 10 or 12 layers.

According to a further preferred method, therefore, within the method step c), folding-in of both folded edges constituted in method step b) is performed to constitute two enclosing edges. In particular, symmetrical folding-in is performed.

In an alternative method, within the method step c), in particular, symmetrical folding-in of the two folded edges formed in method step b) can be performed to constitute two enclosing edges and to constitute two abutting edges.

In a further alternative method, within the method step c), a folded edge is folded in onto the other folded edge along a third fold line lying parallel with a cut edge B.

In particular, a method is to be provided to manufacture a compress with square contact surfaces F with an area of $d^2$, where d is the edge length of a marginal edge D of the compress. In this method, a rectangular material section with the cut edges A and B is preferably used as the initial material, wherein this material section further preferably has an edge length a where a=4d+2e of the cut edges A and an edge length b where b=d+2e' of the cut edges B, where d is the edge length of the final folded compress, e is the edge length of a partial section of the cut edge A where e≦½d and e' is the edge length of a partial section of the cut edge B where e'≦½ d. In this way, by precise folding without any great quantity of off-cuts or waste, an at least 8-ply and no more than 10-ply or 12-ply compress can be provided that exhibits especially even distribution of the material over the contact surface.

The method described here is a method that ensures low-cost manufacture of a medical compress.

It must be emphasized at this point that the characteristics described here of the preferred or alternative embodiments of the inventions are not limited to the individual preferences or alternatives. Rather, the combination of embodiments and the combination of individual characteristics of the alternative forms are equally part of the invention. Nor is the invention to be seen as reduced to the following description of the drawings.

DESCRIPTION OF THE PREFERRED EMBODIMENT

Figure 1:
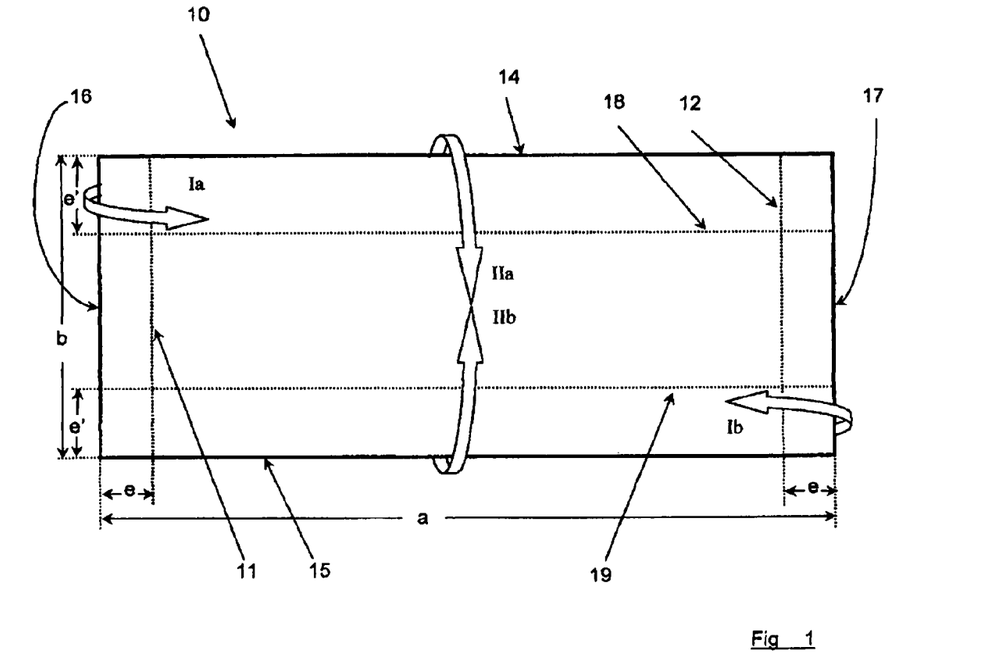
FIG. 1: A material section for the manufacture of an inventive compress viewed from above

FIG. 1 shows a rectangular material section (10) of gauze according to DIN EN 14079 for the manufacture of an inventive compress with square contact surfaces. This material section has two first cut edges A (14, 15) lying opposite each other with the edge length a=230.0 mm. The material section also has two second cut edges B (16, 17) lying opposite each other with the edge length b=99.0 mm.

A method for the manufacture of an at least 8-ply compress is explained below using drawings. In a first method step, the rectangular material section (10) described is provided. In a second method step, the cut edges B (16, 17) are folded over in the direction of the arrows Ia and Ib along the fold lines I (11, 12) to constitute first folded edges G (26) and G' (27) on the upper side of the material section. Folding over a cut edge B (16, 17) results in two subunits of the material section being placed one upon the other such that the folded-over subunit and also the remaining subunit each form a separate layer, wherein the layers formed are directly adjacent and are connected by the folded edges G (26) or G' (27) that are formed. The distance e of each of the fold lines I from the parallel cut edge B that is nearer to it is e=14.5 mm in each case. In a third method step, the cut edges A (14, 15) are then folded over in the direction of the arrows IIa and IIb along the fold lines II (18, 19) to form second folded edges H (24) and H' (25) on an upper side of the material section. The distance e' of each of the fold lines II (18, 19) from the parallel cut edge A that is nearer to it is 24.5 mm in each case. By folding over the cut edges A (14, 15), the second folded edges H (24) and H' (25) are formed, wherein each of these folded edges H or H' comprises two regions at a distance from each other, that are constituted as an enclosing edge (33*a*, 33*b*, 33*a*', 33*b*'). Moreover, from the partial regions of the cut edges A, abutting edges (28*a*, 29*a*; 28*b*, 29*b*; 28*b*', 29*b*') are formed.

Figure 2A:
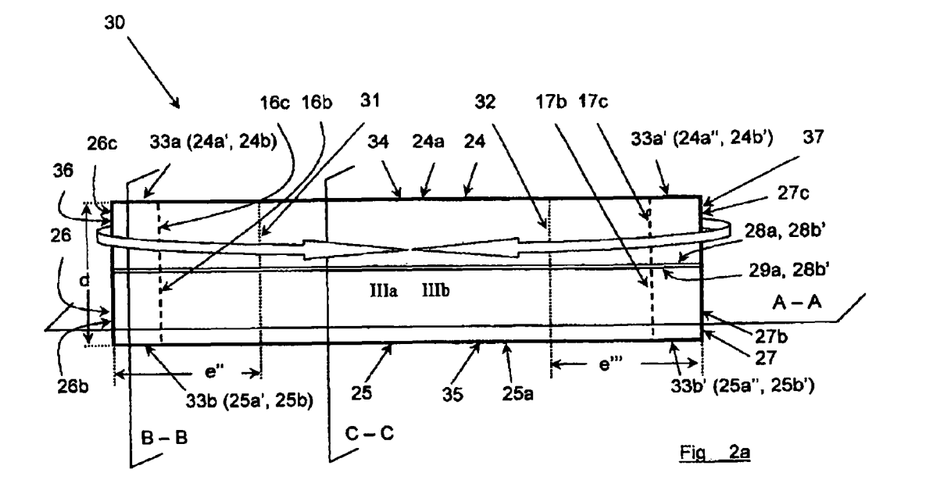
FIG. 2*a*: First intermediate product in the manufacture of an inventive compress viewed from above
Figure 2B:
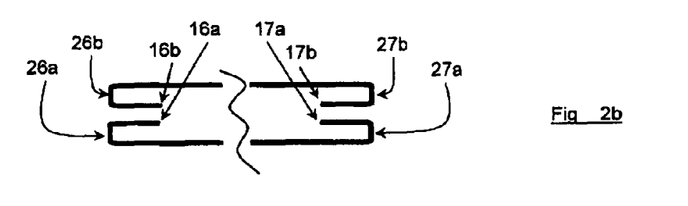
FIGS. 2*b*, 2*c*, 2*d*: Intermediate product according to FIG. 2*a* in different sectional views
Figure 2C:
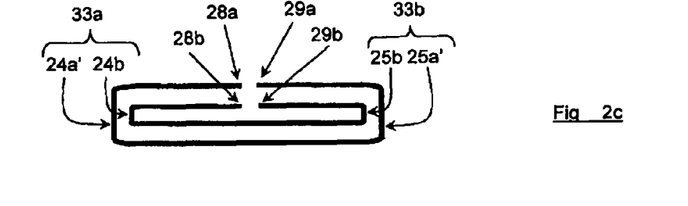
Figure 2D:
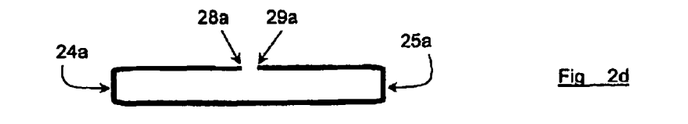

FIG. 2*a* shows the intermediate product A (30) obtained after the third method step with the marginal edges bb (36) and bb' (37) lying parallel with the cut edges B (16, 17) and the marginal edges aa (34) and aa' (35) that are parallel with the cut edges A (14, 15). The marginal edge aa (34) is formed by a partial section (24*a*) of the second folded edge H (24) and by the enclosing edges (33*a*, 33*a*') formed from further partial sections (24*a*', 24*b*, 24*a*", 24*b*') of folded edge H (cf. also FIG. 2*c*—sectional view of the intermediate product A along the section line B-B and FIG. 2*d*—sectional view of the intermediate product A along the section line C-C). In analog fashion, the marginal edge aa' (35) is formed by a partial section (25*a*) of the second folded edge H' (25) and by the enclosing edges (33*b*, 33*b*') formed by further partial sections (25*a*', 25*b*, 25*a*", 25*b*') of the folded edge H'. The marginal edge bb (36) is formed by superposed partial sections (26*a*, 26*b*, 26*c*) of the first folded edge G (26) and the marginal edge bb' (37) by superposed partial sections (27*a*, 27*b*, 27*c*) of the first folded edge G' (27) (cf. FIG. 2*b*—sectional view of the intermediate product A along the section line A-A). By folding over the cut edges A (14, 15), abutting edges (28*a*, 29*a*; 28*b*, 29*b*; 28*b*', 29*b*') are formed by the cut edges A, wherein these abutting edges are each spaced at 1.0 mm. All partial regions of the cut edges B (16*a*, 16*b*, 16*c*, 17*a*, 17*b*, 17*c*) are covered by material regions lying on top of them (in the figures the edges covered by material layers lying on top are represented by dashed lines).

In a further method step, the intermediate product A (30) is further processed. For this purpose, the formed marginal edges bb (36) and bb' (37) of the intermediate product A (30) are folded over in the direction of the arrows IIIa and IIIb along the fold lines III (31, 32) to form further abutting edges (38*a*, 39*a*, 38*b*, 39*b*) of the intermediate product onto an upper side of the material section. The distance e" of the first fold line III (31) from the nearest parallel marginal edge aa (36) is e"=50.0 mm. The distance e'" of the second fold line III (32) from the nearest parallel marginal edge aa' (37) is also e'"=50.0 mm. Symmetrical folding-over of the marginal edges aa (36) and aa' (37) is thus performed in this method step. By folding over the marginal edges bb (36) and bb' (37), the enclosing edges I (41) and I' (42) and the abutting edges of the intermediate product B (38*a*, 39*a*, 38*b*, 39*b*, 38*c*, 39*c*) are formed. In this case, each abutting edge of the intermediate product (38*a*, 39*a*, 38*b*, 39*b*, 38*c*, 39*c*) is formed from partial sections of the folded edges G (26) and G' (27) so that the abutting edges connect directly adjacent layers. No further layers are inserted or interposed between the connected layers.

Figure 3A:
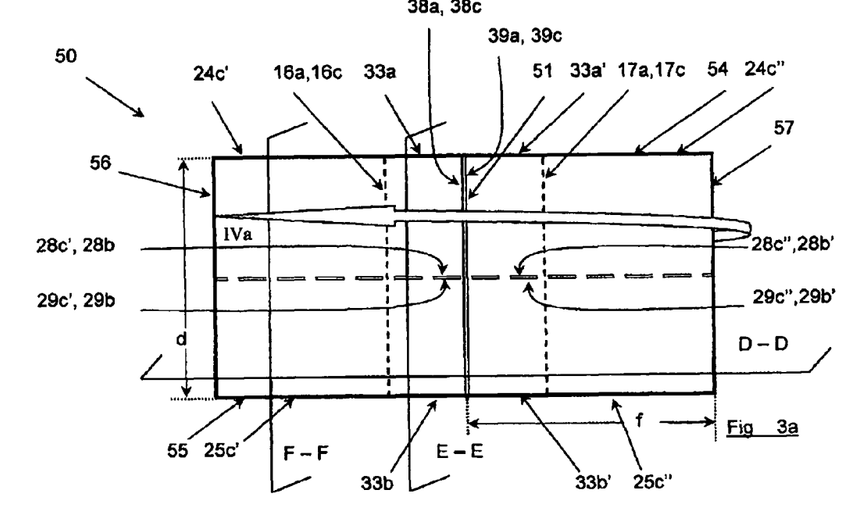
FIG. 3*a*: A second intermediate product for the manufacture of an inventive compress viewed from above
Figure 3B:
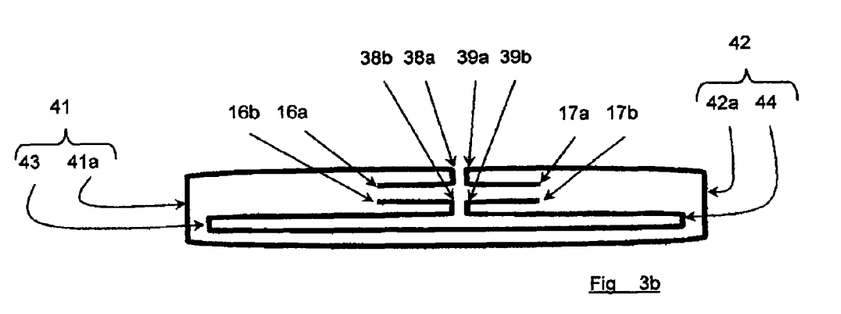
FIGS. 3*b*, 3*c*, 3*d*: Intermediate product according to FIG. 3*a* in different sectional views
Figure 3C:
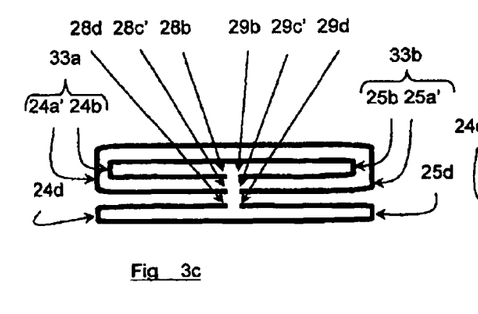
Figure 3D:
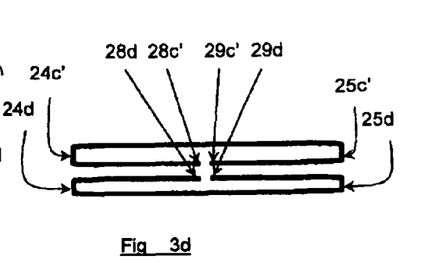

FIG. 3*a* shows an intermediate product B (50) obtained by the fourth method step with the marginal edges bbb (56) and bbb' (57) parallel with the cut edges B and the marginal edges aaa (54) and aaa' (55) parallel with the cut edges A. In this case, the marginal edge aaa (54) is formed by superposed partial sections of the second folded edge H (24*d*, 24*c*', 24*c*") and by the enclosing edges (33*a*, 33*a*') formed in the third method step (cf. also FIG. 3*c*—sectional view of the intermediate product B along the section line E-E; and FIG. 3*d*—sectional view of the intermediate product A along the section line F-F). In analog fashion, the marginal edge aaa' (55) is formed by superposed partial sections of the second folded edge H' (25*c*', 25*d*, 25*c*") and by the enclosing edges (33*b*, 33*b*') formed in the third method step. The marginal edge bbb (56) is formed by the enclosing edge I (41) and, in analog fashion, the marginal edge aaa' (57) is formed by the enclosing edge I' (42) (cf. FIG. 3*b*—sectional view of the intermediate product B along the section line D-D). In this case, each inside folded edge (43, 44) is enclosed by each outside folded edge (41*a*, 42*a*). Each inside folded edge is directly in contact with the associated outside folded edge, leaving no distance between them. The intermediate product B has abutting edges (28*c*', 29*c*', 28*c*", 29*c*", 28*b*, 29*b*, 28*b*', 29*b*') formed from the cut edges A or from partial sections thereof that are parallel with the marginal edges aaa (54) and aaa' (55). In a further plane of the intermediate product B, further abutting edges (28*d*, 29*d*) are formed from further partial sections of the cut edges A. These abutting edges lie directly against one another, wherein a distance of 1.0 mm must be left between them. The abutting edges (38*a*, 39*a*, 38*b*, 39*b*) formed from the folded edges G and G' also have a distance of 1.0 mm. Both the cut edges B or each partial section (16*a*, 16*b*, 16*c*, 17*a*, 17*b*, 17*c*) and each abutting edge (28*b*, 29*b*, 28*c*', 29*c*', 28*c*", 29*c*", 28*d*, 29*d*, 28*b*', 29*b*') formed from a partial section of the cut edges A are covered by material layers lying on top. There are therefore no exposed cut edges in this intermediate product B (50).

In a last method step, the intermediate product B (50) is further processed. The previously marginal edge bbb' (57) of the intermediate product B (50) previously formed by the enclosing edge I' (42) is folded over in the direction of the arrow IVa along fold line IV (51), so that the folded-over marginal edge bbb' (57) is placed on the marginal edge bbb (56) of the intermediate product B (50) formed by the enclosing edge I. The distance of the fold line IV (51) from the marginal edge bbb (56) corresponds to f=50.5 mm. The fold line IV (51) therefore lies exactly between a pair of abutting edges (38*a*, 39*a*; 38*b*, 39*b*; 38*c*, 38*c*). By this method step, the further folded edges J (47*a*) and J' (46*a*) are formed along the fold line IV (51). The folded edges G and G' forming the abutting edges (38*a*, 39*a*; 38*b*, 39*b*; 38*c*, 39*c*) of the intermediate product B (50) and their partial regions (26*a*, 26*b*, 27*a*, 27*b*, 26*c*, 27*c*) are only placed against the folded edge J' (46*a*). Between each of the partial regions of the folded edges G or G' and the folded edge J' (46*a*), no distance is left so that the participating edges are located directly against one another. In this way, the enclosing edge K' (46) is also formed in this method step.

Figure 4A:
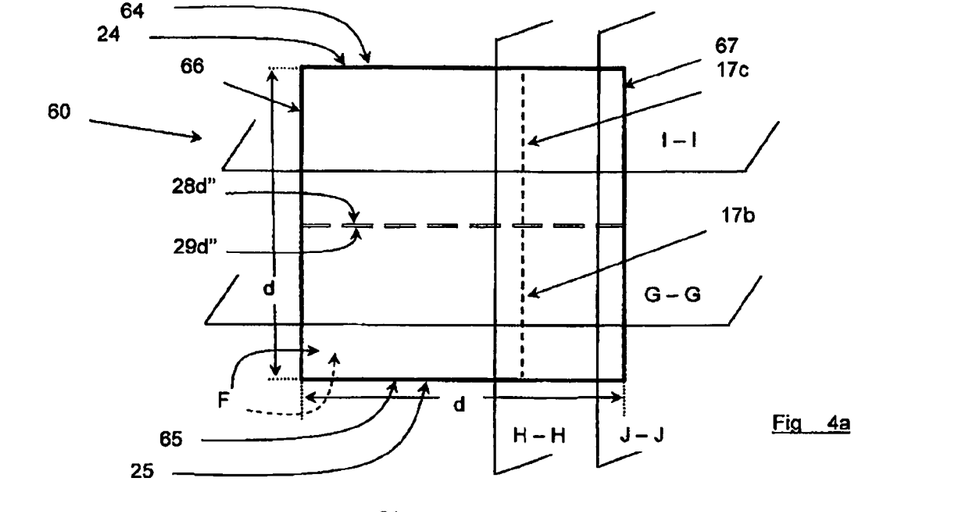
FIG. 4*a*: An inventive compress viewed from above

FIG. 4*a* shows the compress (69) made by the previously described method. The compress with the four equally long marginal edges D', D", D'" and D"" (64, 65, 66 and 67) with an edge length d=50.0 mm has square contact surfaces F with an area of $d^2$=25.0 cm$^2$. All partial regions of the cut edges B and all partial regions of the cut edges A are covered by further layers of material. In FIG. 4*a*, only the upper partial regions of the cut edge B (17*b*, 17*c*) and the upper partial regions of the cut edges A (28*d*", 29*d*") formed as abutting edges are shown. The abutting edges (28*d'''*, 29*d''*) formed from a partial region of the folded edge H (24) and a partial region of the folded edge H' (25) are located directly against one another, wherein the distance between them is 1.0 mm. This corresponds to a distance of 2% with reference to any marginal edge of the final folded compress (all edges are of equal length). The second cut edges B or partial sections thereof (16*a*, 16*b*, 16*c*, 17*a*, 17*b*, 17*c*) lie coextensively one upon the other, wherein the distance from the first parallel marginal edge D' (67) is 14.5 mm at every point. This corresponds to 29% of the length of a second marginal edge D" (64) that is perpendicular to the first marginal edge.

Figure 4B:
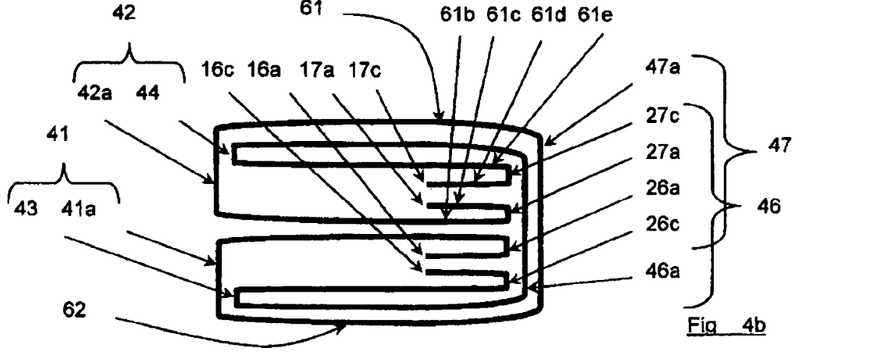
FIGS. 4*b*, 4*c*, 4*d*, 4*e*: The compress according to FIG. 4*a* in different sectional views
Figure 4C:
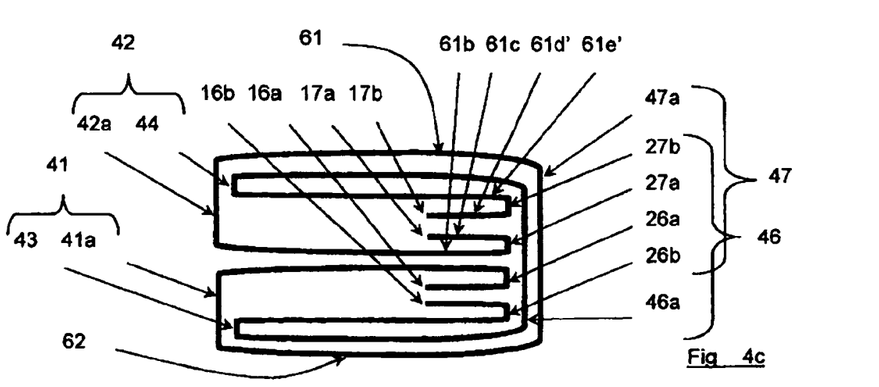
Figure 4D:
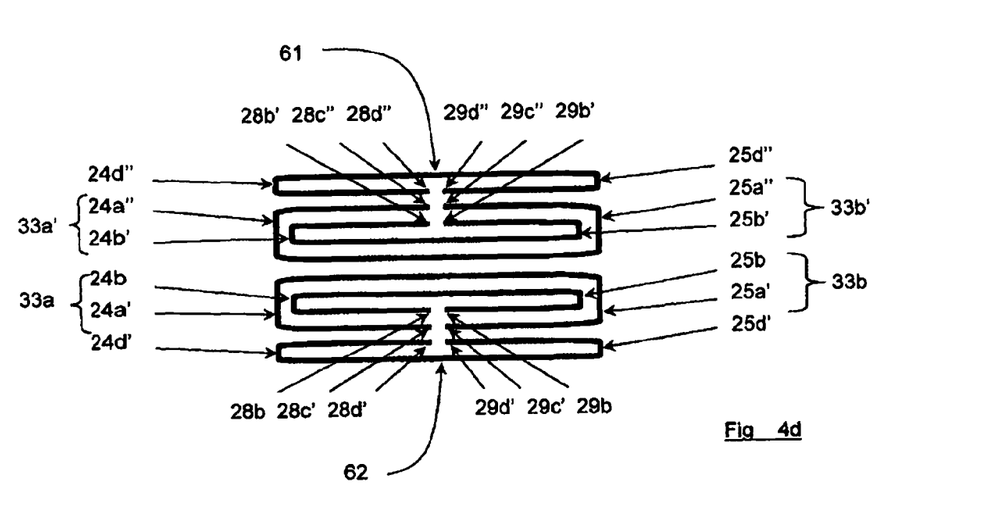
Figure 4E:
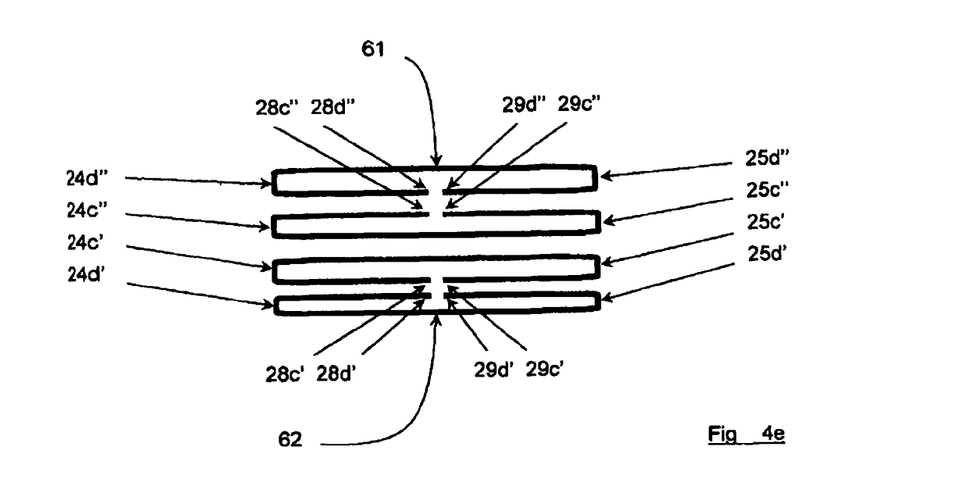

The following FIGS. 4*b*, 4*c*, 4*d*, and 4*e* illustrate the layer structure of the compress (60) and the enclosing edges last formed, wherein FIG. 4*b* shows a sectional view along section line I-I, FIG. 4*c* a sectional view along section line G-G, FIG. 4*d* a sectional view along section line J-J and FIG. 4*e* a sectional view along section line H-H. To illustrate the individual layers and the folded edges enclosing one another—as in all sectional drawings—they are shown pulled apart and spaced out. In particular, it is shown that the two outer layers (61, 62) forming the contact surfaces F are connected by the folded edge J (47*a*). These layers are each formed by contiguous areas of the material section. Each further layer is enclosed by these two outer layers, so that all further layers lie between the outer layers (61, 62).

Moreover, the enclosing edge K (47) that forms the first marginal edge D' of the compress is shown. The enclosing edge K (47) is formed from the inside folded edges G and G' or the partial sections thereof (26*a*, 26*b*, 27*a*, 27*b*, 26*c*, 27*c*) and the outside folded edge J (47*a*), wherein the inside folded edges are held at a distance from the outside folded edge by the further folded edge J' (46*a*), which also forms an enclosing edge K' (46) with the inside folded edges. Because the distance corresponds to the thickness of the material used, which is less than 0.5 mm, the distance is negligible, so that the inside edges are also located directly against the outside folded edge. Each of the inside folded edges G or G' or the partial sections thereof (26*a*, 26*b*, 27*a*, 27*b*, 26*c*, 27*c*) connects two directly adjacent layers or partial sections of the layers (cf. FIGS. 4*b* and 4*c*). For example, the first partial sections (27*b*, 27*c*) of the folded edge G' (27) each connect a partial section of the third layer (61*e*, 61*e'*) with a partial section of the fourth layer (61*d*, 61*d'*) of the compress. A further partial section (27*a*) connects the fifth layer (61*c*) with the sixth layer (61 *b*) of the compress. The abutting edges (28*d'''*, 29*d'''*) formed from the cut edges A and further abutting edges (28*c'*, 29*c'*; 28*c''*, 29*c''*; 28*d'*, 29*d'*; 28*b*, 29*b*; 28*b'*, 29*b'*) formed from the cut edges A or the partial sections thereof are perpendicular to the enclosing edge K (47) or K' (46).

It is also shown that the second marginal edge D" (64) of the compress is formed from superposed partial sections of the folded edge H (24*c'*, 24*d'*, 24*c''*, 24*d''*) and the enclosing edges (33*a*, 33*a'*) formed in the third method step, the third marginal edge D''' (45) from superposed partial sections of the folded edge H' (25*c'*, 25*d'*, 25*c''*, 25*d''*) and the enclosing edges (33*b*, 33*b'*) formed in the third method step, and the fourth marginal edge D'''' (66) from the superposed enclosing edges I (41) and I' (42). All superposed edges are coextensive as seen from above. The compress thus only has marginal edges that are formed by folded edges or enclosing edges. In particular, no cut edges of the material section (10) constitute a marginal edge of the compress (60). Each layer of this compress is connected by at least one folded edge to a further layer of the compress, wherein the compress has a first and a second marginal region when viewed in cross-section. The first marginal region is 8-ply, while the second marginal region is 12-ply. The four additional layers in the second marginal region are obtained by folding over the cut edges B (16, 17) (cf. FIG. 4*b*, 4*c*).

As an 8-ply compress, this compress has no exposed cut edges even if it is unfolded once (cf. FIG. 3*a*). This compress could therefore be used either as a 4-ply or 8-ply compress. The compress (60) has a thickness of 1.12 mm in the first marginal region (8 layers) and a thickness of 1.36 in the second marginal region (12 layers), each measured at a test pressure of 2 g/cm$^2$ (cf. below). In this way, a plurality of these compresses can easily be stacked because they have an even distribution of materials over all areas.

A comparison of the stack heights is given below. For example, if folded-edge compresses available on the market (folded-edge compresses 5×5 cm—Paul Hartmann AG) are stacked, the pack with a stack of 100 compresses has a height of 155 mm (outer dimension of the packaging). If, on the other hand, 100 inventive compresses (60) are stacked and packaged under the same conditions with the same packaging material, the outer dimension is 139 mm (the same measurement conditions). This corresponds to a reduction in stack height of approx. 10%.

For a partial stack of 5 compresses or each individual compress, the following values result, wherein a test pressure of 2 g/cm$^2$ was complied with. Each compress is folded identically and the compresses in the stack are stacked coextensively.

|  |  | Thickness (5 compresses)/ mm | Thickness (1 compress)/ mm |
| --- | --- | --- | --- |
| Folded-edge compresses (Paul Hartmann AG) | Marginal edge (16 layers) | 8.10 | 1.62 |
|  | Parallel opposite edge (8 layers) | 5.65 | 1.13 |
| Inventive compresses (60) | First marginal region (8 layers) | 5.60 | 1.12 |
|  | Second marginal region (12 layers) | 6.81 | 1.36 |

By the configuration of the folded edges, a stack of compresses can be provided that is more stable than compresses available on the market and occupies less space.

The following table provides examples of square compresses that are formed according to the method described above from a rectangular material section with two parallel cut edges A located opposite each other and two parallel cut edges B located opposite each other. The edge length a of the cut edges A is greater than the edge length b of the cut edges B of the material section provided. The compresses being compared have the stated marginal edge length d in their final folded condition. The table is intended to illustrate the extent to which, if the same material is used, a material saving can be achieved over known folded-edge compresses—Paul Hartmann AG (1st fold).

| Surface of the material section used | Compress 1 d = 5 cm | | | Compress 2 d = 7.5 cm | Compress 3 d = 10 cm |
|---|---|---|---|---|---|
| $F_M = a \cdot b$ | e = 1.0 cm | e = 1.5 cm | e = 2.0 cm | e = 1.5 cm | e = 1.5 cm |
| 1st fold folded-edge compress $F_M = 4d \cdot (2d + 2e)$ | 240 cm² | 260 cm² | 280 cm² | 540 cm² | 920 cm² |
| 2nd fold (according to the invention) $F_M = (4d + 2e) \cdot 2d$ | 220 cm² | 230 cm² | 240 cm² | 495 cm² | 860 cm² |
| Material saving | 20 cm² (9.1%) | 30 cm² (11.5%) | 40 cm² (14.3%) | 45 cm² (8.3%) | 60 cm² (6.5%) |

For example, the material saving for an inventive compress with square contact surfaces and an edge length d where d=5 cm (compress 1) with an identical width e of the section folded over in the first step where e=1.5 cm is approx. 11.5% as compared with established folded-edge compresses. Both the abutting edges and the enclosing edges of the inventive compresses do not exhibit spacing. The material saving can therefore be achieved by precise folding in a novel way, wherein an inventive enclosing edge is achieved in the compress by folding.

The medical compresses shown here can, in particular, be used in emergency medicine and also in surgical interventions. They are characterized by special safety of use and by an especially even distribution of material.

We claim:

1. A medical compress comprising:
   at least 8 layers of a textile web material, wherein each layer is connected to a further layer by at least one folded edge, and at least two folded edges are perpendicular to each other, the compress constructed from a rectangular material section of a web material, said rectangular material section having two parallel first cut edges located opposite each other and two parallel second cut edges located opposite each other, wherein a first edge length of said first cut edges is greater than a second edge length of said second cut edges, the compress being folded to generate an enclosing edge formed from at least one first folded edge and one second folded edge, wherein said first folded edge directly connects adjacent layers or partial sections of directly adjacent layers and is parallel to said second cut edges, said second folded edge connecting outer layers forming contact surfaces of the compress.

2. The medical compress of claim 1, wherein said enclosing edge comprises at least two first folded edges connecting directly adjacent layers.

3. The medical compress of claim 2, wherein said enclosing edge comprises at least four first folded edges connecting directly adjacent layers.

4. The medical compress of claim 1, wherein the compress is folded in such a way that the outer layers forming the contact surfaces of the compress are each completely constituted by a contiguous area of the web material.

5. The medical compress of claim 1, wherein partial sections of said second cut edges are disposed so as to be completely coextensive within the compress when the compress is viewed from above.

6. The medical compress of claim 1, wherein the second cut edges or a partial section of said second cut edges have, at every point, a distance from said enclosing edge of at least 20% and no more than 80% of a length of a marginal edge that is perpendicular to that enclosing edge.

7. The medical compress of claim 1, wherein each marginal edge of the compress is constituted exclusively by folded edges or enclosing edges.

8. The medical compress of claim 1, wherein the compress comprises two cut or folded edges as abutting edges.

9. The medical compress of claim 1, wherein the compress is folded in such a way that said first cut edges or partial regions of said first cut edges are constituted as abutting edges.

10. The medical compress of claim 1, wherein the compress has a first 8-ply marginal region and a second 12-ply marginal region, as seen in cross-section.

11. A stack of compresses comprising a plurality of the compresses of claim 1.

12. A method for manufacturing a medical compress having at least 8 layers of a textile web material, the method comprising the steps of:
   a) providing a rectangular material section of the web material with two first cut edges lying opposite each other and two second cut edges lying opposite each other, wherein a first edge length of the first cut edge is larger than a second edge length of the second cut edge;
   b) folding in the second cut edges of the rectangular material section along a first fold line parallel to the second cut edge and along a second fold line parallel to the second cut edge to generate two first folded edges;
   c) folding in at least one of the folded edges generated in step b) along a third fold line lying parallel to the second cut edge to generate a further folded edge;
   d) folding in the folded edge or the enclosing edge generated in step c) along a fourth fold line lying parallel to the second cut edge to generate an enclosing edge that comprises at least a first folded edge and a second folded edge; and
   e) further folding in of cut edges, formed folded or folded in edges to generate abutting edges, further folded or folded in edges, wherein each layer of the compress is connected to a further layer by at least one folded edge and at least two folded edges are perpendicular to each other.

13. The method of claim 12, wherein folding in of the first cut edges of the rectangular material section is effected to constitute two abutting edges.

14. The method of claim 13, wherein the first cut edges are symmetrically folded.

15. The method of claim 13, wherein, in method step c), folding in of the two folded edges constituted in method step b) is effected to constitute two enclosing edges.

16. The method of claim 15, wherein the two folded edges constituted in step b) are symmetrically folded in.

17. The method of claim 14, wherein, in method step c), symmetrical folding in of the two folded edges constituted in method step b) is effected to constitute two enclosing edges and to constitute two abutting edges.

18. The method of claim 17, wherein the two folded edges constituted in method step b) are symmetrically folded in.

19. The method of claim 12, wherein, in method step c), a folded edge is folded in onto an other folded edge along a third fold line lying parallel to the second cut edge.

20. The method of claim 12, wherein, in method step b), the first cut edges of the rectangular material section are folded in, wherein each fold line is at a distance of at least 5 mm and no more than 30 mm from a nearest second cut edge at every point.

* * * * *